United States Patent [19]

Blikken

[11] Patent Number: 5,191,892
[45] Date of Patent: Mar. 9, 1993

[54] ESOPHAGEAL/STETHOSCOPIC GASTRIC TUBE

[76] Inventor: Wayland G. Blikken, 69 Bay Circle Dr., Holland, Mich. 49424

[21] Appl. No.: 757,269

[22] Filed: Sep. 10, 1991

[51] Int. Cl.$^5$ .............................................. A61B 5/02
[52] U.S. Cl. .................................. 128/715; 128/773; 604/54; 604/268
[58] Field of Search ...................... 128/715, 642, 773; 604/54, 268

[56] References Cited

U.S. PATENT DOCUMENTS

| | | | |
|---|---|---|---|
| 3,734,094 | 5/1973 | Calinog | 128/642 |
| 3,982,540 | 9/1976 | Ross | 604/268 |
| 4,613,323 | 9/1986 | Norton et al. | 624/54 |
| 4,735,607 | 4/1988 | Keith, Jr. | 604/54 |
| 4,917,107 | 4/1990 | Bell et al. | 128/715 |

Primary Examiner—Lee S. Cohen
Assistant Examiner—Jeffrey R. Jastrzab
Attorney, Agent, or Firm—Barnes, Kisselle, Raisch, Choate, Whittemore & Hulbert

[57] ABSTRACT

An esophageal gastric tube inserted through the mouth or nose into the stomach of a patient. The single tube incorporates a lumen ending in a stomach catheter to permit necessary evacuation of the stomach contents including a relief passage to admit ambient air pressure to avoid undue stomach contraction. The tube also incorporates a stethoscopic lumen with a pick-up port to be located in the heart lung area of the patient to monitor heart and lung sounds during an on-going operation.

3 Claims, 1 Drawing Sheet

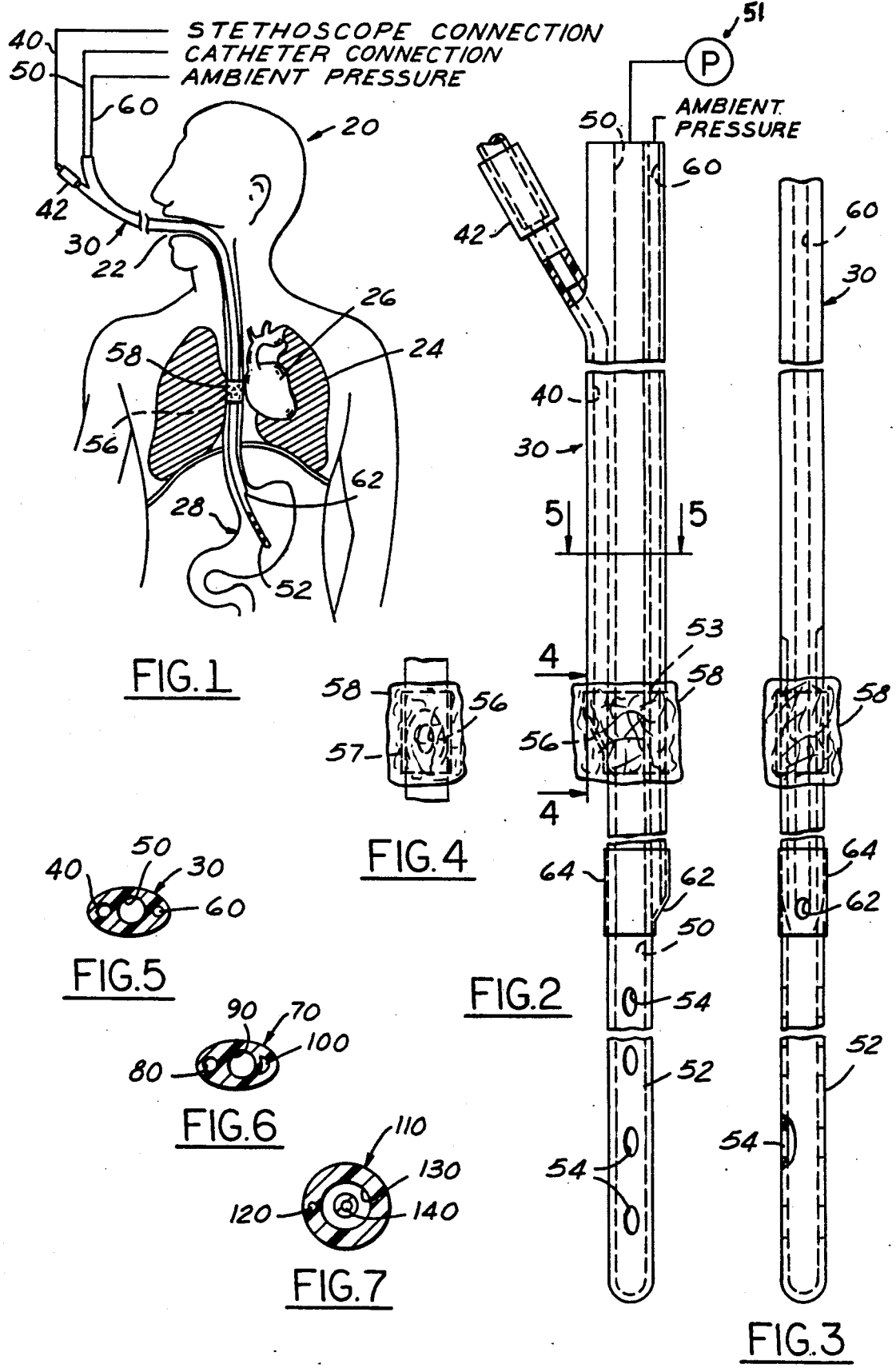

ESOPHAGEAL/STETHOSCOPIC GASTRIC TUBE

FIELD OF INVENTION

The use of oral or nasal esophageal tube introduction to monitor heart and breath sounds of a patient in conjunction with gastric tubes to control evacuation of the stomach.

BACKGROUND AND FEATURES OF THE INVENTION

In scheduled surgical procedures, particularly those involving general anesthesia, a patient is instructed to refrain from eating or drinking for a prescribed period. This insures that, in the event of nausea and vomiting, the danger of stomach contents reaching the lungs and concomitant pneumonia is minimized. Also, during such operations, it is common practice to introduce an esophageal stethoscope which will allow the anesthetist or anesthesiologist to monitor continuously patient's heart and breath sounds.

In addition, a gastric tube is frequently used, again through a nasal or oral route, to decompress or evacuate the stomach to prevent post-operative nausea or vomiting. This is especially important for emergency operations where there has been no pre-operative fasting.

Where tubes are installed through the nasal or oral routes, there is always a risk of perforation of the nasopharynx or esophagus and thus the danger of morbidity or even death. It is the object of the present invention to provide an apparatus which will combine the monitoring into a single unit which will have the following advantages:

(1) Decrease the risk of perforation during installation,
(2) Decrease the risk of aspiration pneumonia (a potentially lethal combination),
(3) Increase patient comfort by decreasing post-operative nausea and vomiting,
(4) Decrease the time factor in installations and thus the cost factor as a result of the single insertion with increased simultaneous monitoring,
(5) Promote the use of gastric suctioning as a routine practice during general anesthesia.
(6) Requires no special training for a skilled anesthetist/anesthesiologist.

Various other objects and features will be apparent in the following description and claims in which details of the invention are set forth to enable those skilled in the art to practice the invention, all in connection with the best mode presently contemplated for the invention.

BRIEF DESCRIPTION OF THE DRAWINGS

DRAWINGS accompany the disclosure and the various views thereof may be briefly described as:

FIG. 1, a diagrammatic view of the instrument installed in a human body.

FIG. 2, a view of the instrument in lineal form showing the various lumens incorporated in the instrument.

FIG. 3, a side view of the instrument displayed in FIG. 2.

FIG. 4, a partial side view of the instrument at lines 4—4 of FIG. 2.

FIG. 5, a section on line 5—5 of FIG. 2.

FIG. 6, a modified section as an alternate tube design.

FIG. 7, a second modification of a composite coaxial tube design.

DETAILED DESCRIPTION OF THE INVENTION AND THE MANNER AND PROCESS OF USING IT

In FIG. 1, a diagrammatic view depicts portions of a human body including the head 20 and mouth 22, lungs 24, heart 26 and stomach 28.

The instrument is formed as a three-lumen tube 30 illustrated in FIGS. 2, 3 and 5. The section of FIG. 5 shows a stethoscopic lumen 40 which branches off at the top of the tube 30 to a stethoscope connection 42. A central lumen 50 leads to the stomach catheter 52 which is provided with oval ports 54. The stethoscopic lumen 40 and an included pick-up terminates at 56 in a fitting 57 adjacent the heart 26 where a stethoscopic signal in lumen 40 can respond to the sounds of the heart beat and the breathing of a patient (FIG. 2). The opening at 56 is surrounded by an acoustical pick-up membrane 58 which is liquid impervious but does not muffle the sound.

As indicated, the catheter 52 extends into the stomach well beyond the stethoscope pick-up 56 which is adjacent the heart. The lumen 50 will be connected to a vacuum source, shown diagrammatically at 51, to clear the stomach of any contents. It will be appreciated, however, that a vacuum in the stomach could result in an inability to evacuate contents. Accordingly, a third lumen 60 (FIG. 5) is connected to ambient pressure to relieve the negative pressure in the stomach. This lumen 60 opens at 62 in a fitting 64 above the distal end of the catheter 52 and this lumen 60 and opening 62 admits air at ambient pressure (essentially atmospheric) to prevent the existence of negative pressure in the stomach.

Thus, it will be seen that the introduction of a single tube 30 through the nasal route or mouth can provide the anesthetist with a stethoscopic pick up for heart and breathing sounds and also provide a catheter for stomach evacuation and negative pressure relief at the same time.

In FIG. 6, a modified tube 70, which could be an extrusion, has a stethoscopic lumen 80, a main catheter connection lumen 90, and am ambient pressure relief lumen 100. In FIG. 7, a coaxial tube 110 has a stethoscopic lumen 120, a main catheter lumen 130, and an ambient pressure tube 140.

What is claimed is:

1. An instrument for use during surgical operations in which a general anesthetic is administered, comprising a composite multi-lumen tube having a proximal end and a distal end for nasal or oral introduction into the esophagus, said tube having a main lumen extending from the proximal end of the tube and ending in a catheter at a distal end to be located in the stomach, means at the proximal end of the main lumen for connection to a negative pressure source, a second lumen having a proximal end and a distal end positioned lineally of the composite tube having a distal end in the general area of the heart and lung when inserted, a stethoscopic pick-up in said second lumen adjacent its distal end, a stethoscopic connection connected to the pick up at the proximal end of the composite tube, and a third lumen having a proximal end and a distal end co-lineal with said first and second lumens extending from an atmospheric opening at the proximal end of the composite tube to a distal vent opening positioned proximal to the catheter between the distal end of the main lumen and the stethoscopic pick-up to be open to the stomach to relieve negative pressure.

2. An instrument as defined in claim 1 in which said composite tube is an extruded member with said lumens extending co-lineally from the proximal end to the respective distal ends.

3. An instrument as defined in claim 1 in which an acoustical, liquid impervious, pick-up membrane is positioned to surround the stethoscopic pick-up at the distal end of the second lumen.

* * * * *